United States Patent
Daussin et al.

(10) Patent No.: US 9,045,395 B2
(45) Date of Patent: Jun. 2, 2015

(54) PROCESS FOR THE PRODUCTION OF ALIPHATIC ISOCYANATES

(71) Applicant: Dow Global Technologies LLC, Midland, MI (US)

(72) Inventors: Rory D. Daussin, Spring, TX (US); Paula A. Cameron, Pearland, TX (US); Lao-Jer Chen, Sugar Land, TX (US); Jorge Jimenez, Lake Jackson, TX (US); Joerg-Peter Gehrke, Stade (DE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/887,621

(22) Filed: May 6, 2013

(65) Prior Publication Data
US 2013/0245314 A1    Sep. 19, 2013

Related U.S. Application Data

(63) Continuation of application No. 12/775,715, filed on May 7, 2010, now Pat. No. 8,455,695.

(60) Provisional application No. 61/175,878, filed on May 6, 2009.

(51) Int. Cl.
*C07C 263/10* (2006.01)
*C07C 263/14* (2006.01)
*C07C 265/14* (2006.01)

(52) U.S. Cl.
CPC ............ *C07C 263/10* (2013.01); *C07C 265/14* (2013.01)

(58) Field of Classification Search
USPC .......................................... 560/347
See application file for complete search history.

(56) References Cited

U.S. PATENT DOCUMENTS

| 2,642,449 A | 6/1953 | Morningstar et al. |
| 7,045,573 B2 * | 5/2006 | Mayer et al. ................. 524/840 |
| 2010/0048770 A1 * | 2/2010 | Burckhardt ................... 524/47 |

FOREIGN PATENT DOCUMENTS

| GB | 1050555 A | 12/1966 |
| GB | 1086782 A | 10/1967 |
| JP | 55-8845 | 4/1980 |

* cited by examiner

Primary Examiner — Sikarl Witherspoon

(57) ABSTRACT

The present invention is an aliphatic or cycloaliphatic isocyanate obtained form a process comprising the steps of reacting an aliphatic or cycloaliphatic primary amine, with phosgene in the presence of an inert solvent, wherein the initial reaction temperature is between 100 and 130° C. and the temperature is subsequently ramped to 150 to 180° C. during the course of the reaction, the solvent to amine weight ratio is 95:5 to 80:20, the total reaction pressure is maintained between 50 and 350 psig and the amine is rapidly dispersed in the phosgene through injection in a region of high efficiency mixing.

10 Claims, No Drawings

PROCESS FOR THE PRODUCTION OF ALIPHATIC ISOCYANATES

REFERENCE TO RELATED APPLICATIONS

This present application is a continuation application of U.S. application Ser. No. 12/775,715, filed on May 7, 2010, now allowed, which claims priority from U.S. Application No. 61/175,878, filed May 6, 2009; each application is incorporated herein, in its entirety, by reference.

FIELD OF THE INVENTION

This invention relates to an aliphatic or cycloaliphatic isocyanate obtained from a process comprising the reacting of an aliphatic polyamine or its hydrochloride or carbonate with phosgene.

BACKGROUND OF THE INVENTION

Processes to prepare isocyanates by reacting primary amines with phosgene in an inert solvent are known. When the primary amines are aromatic amines, the aromatic amine can be converted with comparative ease to a high purity aromatic isocyanate by contacting the phosgene directly with the aromatic amine in a solvent. In the case of aliphatic amines, the overall reaction with phosgene is relatively slow in comparison, thus undesirable chloroderivative by-products are often formed.

For these reasons, the production of aliphatic isocyanates is usually accomplished in one of two ways. The first method, known as the salt method, involves converting the amine to the hydrochloride or the carbonate. The resulting salt is transformed into the isocyanate by passing phosgene through a solvent/hydrochloride slurry at elevated temperatures. The second method, known as cold-hot base approach, comprises adding the free amine to excess phosgene, preferably condensed in an inert solvent at low temperatures. The resulting slurry is heated while more phosgene is passed through to complete the reaction. Aliphatic diisocyanates have been manufactured using both methods at temperatures ranging from 130 to 175° C. in a variety of inert solvents. At these temperatures, considerable amounts of chloromonoisocyanates are noted to form. Unfortunately, the boiling points of the desired diisocyanates and the chloride impurity derived from them are often found to be quite close, thus rendering separation by distillation difficult.

When aliphatic isocyanates containing the chlorinated impurity are used to prepare polyurethane polymers, the chlorinated impurity is known to adversely affect the desired urethane forming reaction. Consequently, a large amount of work has been compiled detailing process options to reduce the chlorinated impurities obtained during the phosgenation step. GB 1086782 describes a process for the phosgenation of aliphatic amines, or their hydrochloride equivalents, at temperatures of 120 to 180° C. in a weight ration of solvent/amine of 18:1 to 30:1. GB 1050555 discloses a process for preparing an organic isocyanate via phosgenation of a primary amine hydrochloride containing a surface active substance in an inert solvent. JP55-88451A describes the use of a continuous high temperature phosgenation process. U.S. Pat. No. 2,642,449 discloses a process utilizing phosgene injected into the reaction mixture at elevated pressure.

Even when the desired reactions dominate, additional problems are incurred due to the inherent reactivity of aliphatic amines. When either the salt or cold-hot base process is employed, a carbamoyl chloride is formed as an intermediate. The carbamoyl chloride is then subjected to dehydrochlorination so that the aliphatic polyisocyanate is prepared. The dehydrochlorination of the carbamoyl chloride into the polyisocyanate takes place at a low reaction velocity and in general, requires a high reaction temperature of at least 120° C., usually 130° C. or higher. When the polyisocyanate so formed is exposed to heat for a long time, the polyisocyanate tends to become tarry, resulting in a reduction in the production yield. Further, hydrochloric acid gas which has been formed as a result of decomposition of the carbamoyl chloride reacts the resultant polyisocyanate, whereby the carbamoyl chloride is formed again. The carbamoyl chloride becomes tarry at a far higher rate than the polyisocyanate, so that the yield is reduced further.

The processes of the prior art, however, have been largely ineffective when used with amines that have a high degree of symmetry or crystallinity, and isomeric mixtures thereof. Amines of this type generally yield products having high levels of oligomeric and/or intractable content during the phosgenation reaction.

The prior processes have also been cost ineffective in that they require large amounts of solvent, thus incurring extensive distillation and recycling costs. As a result, the conventional processes are not amenable to the commercial production of isocyanates directly from crystalline or ordered amines.

It is an object of the present invention to provide an economical process for preparing an aliphatic or cycloaliphatic isocyanate, more specifically isocyanates based isomeric mixtures containing high levels of a symmetrical or crystalline isomer, in high yields by the phosgenation process.

SUMMARY OF THE INVENTION

In one embodiment, the invention is an aliphatic or cycloaliphatic isocyanate obtained from a process comprising:
  reacting an aliphatic or cycloaliphatic primary amine, or the hydrochloride or carbonate salt thereof, with phosgene in the presence of an inert solvent wherein the initial reaction temperature is between 100 and 130° C. and within 60 minutes of reaching said reaction temperature,
  subsequently increasing the temperature to 150 to 180° C. during the course of the reaction over a time span of about 10 minutes or less,
  maintaining the solvent to amine weight ratio from 95:5 to 80:20,
  maintaining the total reaction pressure between 50 and 350 psig and
  dispersing the amine in the phosgene, preferably wherein the amine is dispersed in the phosgene through injection. Phosgene is preferably used as a co-solvent.

In another embodiment, the invention is a an aliphatic or cycloaliphatic isocyanate obtained from a process comprising:
  reacting an aliphatic or cycloaliphatic amine, or the hydrochloride or carbonate salt thereof, with phosgene in the presence of an inert solvent wherein the reaction is done in two or more sequential reactors,
  maintaining reactor temperature from 100 to 130° C.,
  controlling the solvent to amine weight ration is 95:5 to 80:20, and the total reactor pressure from 50 to 350 psig and
  providing a residence time in the first reactor of less than 5 minutes;

transferring the product from a first reactor into a second reactor, maintaining a temperature in the second reactor from 150 to 180 C, controlling a total second reactor pressure from 50 to 350 psig and providing a residence time in the second reactor of less than 8 hours, preferably wherein the amine is dispersed in the phosgene through injection.

In either embodiment, it is preferred that the aliphatic or cycloaliphatic amine is composed of an isomeric mixture of amines, such as 1,3-, 1, 4-bis(aminomethyl)cyclohexane or an isomeric mixture thereof.

The aliphatic polyamine can be selected from the group consisting of xylylenediamine, hexamethylenediamine, trimethylhexamethylenediamine, 1,6,11-triaminoundecane, bis(aminoethyl)cyclohexane, 1,4-diaminocyclohexane, 1,4-bis(aminoethyl)benzene, m-tetramethylxylylenediamine, p-tetramethylxylylenediamine, 2,4,6-tri(aminomethyl)cyclohexane, isophoronediamine, bis(aminocyclohexyl)methane, 2,2-bis(aminocyclohexyl)propane, bis(aminomethyl)cyclohexane and bis(aminomethyl)norbornene.

The reaction is preferably conducted in an inert liquid medium having a boiling point of 90° C. or higher, preferably a solvent having a donor number greater than 7, especially an organic solvent.

Optionally, either the hydrochloride or carbonate salt of the primary amine may be used.

When phosgene is used as a co-solvent, increased amine concentrations can be used, thereby substantially increasing the yield of the desired isocyanate without incurring the substantial volume requirements of the processes of the prior art.

According to the present invention, an aliphatic or cycloaliphatic isocyanate having extremely low impurity contents can efficiently be obtained in high yield, thereby rendering post treatment steps, such as extensive distillation, unnecessary.

DETAILED DESCRIPTION

This present invention relates to a process for preparing an aliphatic polyisocyanate by reacting an aliphatic polyamine or its hydrochloride or carbonate with phosgene. It has surprisingly been found that in the case of symmetrical or crystalline amines, such as 1,4-bis(aminomethyl)cyclohexane and isomeric mixtures thereof, that low initial reaction temperatures are not advantageous and are, more important, a hindrance to high-yield reactions. Specifically, reaction of bis(aminomethyl)cyclohexanes in dichlorobenzene with phosgene at initial temperature less than about 80 C produces the normal reaction mixture slurry. However, in heating this reaction mixture to higher temperatures in the second phosgenation stage, the amine hydrochloride salts agglomerate into an intractable mass. In addition reaction times are elongated (greater than 10 hours) and overall yields to the bis(isocyanatomethyl)cyclohexane product are less than 75%.

The process of the present invention solves the above-noted problems. According to the present process, phosgene is reacted at increased temperature and pressure to increase the rate of formation of a carbamoyl chloride from a corresponding polyamine and at the same time, the reaction temperature is ramped from the initial 100-130 C to 150-180 C, to accelerate the formation of the carbamoyl chloride without exposing the resultant product to elevated temperatures for prolonged time periods, whereby the aliphatic polyisocyanate is prepared with the equilibrium always biased toward the polyisocyanate side. This process effectively decreases byproduct formation derived from reaction of carbamoyl chloride during the phosgenation reaction and moreover, increases the rate of formation of the aliphatic polyisocyanate. This makes it possible to suppress the conversion of the polyisocyanate into tar and hence obtain the product at a relatively high yield.

The current invention focuses on processes in which the intrinsic phosgene/amine ratio is maintained at high levels during the phosgenation step due to the very slow dissociation rate of said amine hydrochloride. The very high phosgene/amine ratio, in turn, minimizes by-products and thereby leads to high reaction yields. This modification effectively eliminates the additional process step of converting the amine to the hydrochloride salt. It also serves to advantageously reduce the overall reaction cycle time.

It has also been found that initial reaction temperatures of from 100 to about 130 C in a first stage, followed by an increased temperatures in the second stage, e.g. 150 to 180 C, of the phosgenation effectively prevents agglomeration of the initial amine hydrochloride salts. In addition, the increased initial reaction temperatures ultimately decreases the reaction times to less than 8 hours and substantially improved yields to over 80%. Preferably the residence time is reduced to less than 5 hours. More preferably the residence time is reduced to less than 3 hours. Most preferably the residence time is less than 2 hours.

For the phosgenation of 1,4-bis(aminomethyl)cyclohexane, initial elevated temperature mixture and reaction of the amine solution with the phosgene solution provides substantial advantage in consideration of commercial processes for the production of bis(isocyanatomethyl)cyclohexane mixtures.

It has been discovered that high efficiency mixing can effectively distribute the amine solution into the reaction mixture. High efficiency mixing is also necessary to obtain high yields and obtaining a reduced residence time. High efficiency mixing is described in the art, see for example Gary B. Tatterson, "Fluid Mixing and Gas Dispersion in Agitated Tanks," McGraw Hill: New York, N.Y., 1991, the disclosure of which is incorporated herein by reference. High efficiency mixing typically requires very high agitation, >10 hp/1000 gal.

The term "aliphatic or cycloaliphatic polyamine" as used herein includes bifunctional or higher organic amines having an alkane moeity with the amino group bonded thereto. Examples of such compounds include linear aliphatic polyamines such as pentamethylenediamine, hexamethylenediamine, 2,2,4-trimethylhexamethylenediamine, 2,4,4-trimethylhexamethylenediamine, octamethylenediamine, 1,6,11-triaminoundecane and nonamethylenediamine; cyclic polyamines such as bis(aminomethyl)cyclohexane, bis(aminoethyl)cyclohexane, 1,4-diaminocyclohexane, 1,4-bis(aminoethyl)benzene, m-tetramethylxylylenediamine, p-tetraemethylxylylenediamine, 2,4,6-tri(aminomethyl)cyclohexane, isophoronediamine, bis(4-aminocyclohexyl)methane, 2,2-bis(4-aminocyclohexyl)propane, m-xylylenediamine, p-xylylenediamine, o-xylylenediamine, and mixtures of two or more isomers thereof at desired ratios and bis(aminomethyl)norbornene; and amino acid polyamines such as methyl lysinate and aminoethyl lysinate.

The present invention is best suited for the production of symmetrical or crystalline isomers, and isomeric mixtures thereof. In the process of this invention, these aliphatic polyamines are also usable in the form of hydrochlorides or carbonates. Isocyanates obtained from these aliphatic polyamines or the salts thereof will be called "aliphatic polyisocyanates".

The process of the present invention has a primary feature in that phosgene is reacted with an aliphatic polyamine or a salt thereof mixed in a liquid medium at a temperature of 100 to 130° C. and the ramping the temperature to approximately 150 to 180° C., in other words, the reaction is conducted while steadily increasing the temperature.

In the present invention, the solvent is employed to smoothly mix, stir and transfer the raw materials and the reaction mixture so that the aliphatic polyisocyanate can be prepared with ease. The final reaction temperature can be above 180° C., e.g. up to the degradation temperature of the isocyanate.

Total reactor pressure is the pressure above the liquid level in the reactor that is comprised of the partial pressures of the reactor components including HCl (generated during the reaction), phosgene, solvent, diisocyanate, and reaction byproducts. The total reaction pressure is thus primarily a function of reaction mixture composition and temperature. Preferably the total reaction pressure of the present invention is from 50 to 350 psig. Pressures below 50 psig do not allow the use of high temperatures as phosgene concentrations adequate for reaction can not be achieved. Although operational pressures may be as high 350 psig, total reactor pressures in excess of 350 psig may be used without detrimental effects on the reaction; however, excessively high pressures become increasing cost prohibitive.

Solvents used in the process of the present invention are "inert liquid medium" which means an organic solvent which is liquid at room temperature and does not react with materials in the reaction system such as the aliphatic polyamine, the aliphatic polyisocyanate, phosgene, and hydrochloric acid. Preferably the solvents have a donor (DN) value of less than 7 as defined by Gutman (V. Gutman, "Coordination Chemistry in Non-Aqueous Solvents," Springer, Wien: New York, 1968).

Specific examples of the inert liquid medium include hydrocarbons such as benzene, toluene, mixed xylenes, o-xylene, m-xylene, p-xylene, cumene, 2,2,5-trimethylhexane, decane and ethylcyclohexane; halogenated hydrocarbons such as chlorobenzene, o-dichlorobenzene, m-dichlorobenzene, p-dichlorobenzene, 1,2,3-trichlorobenzene, 1,2,4-trichlorobenzene, 1,3,5-trichlorobenzene and o-dibromobenzene; nitrogen-containing compounds such as nitrobenzene, N,N-dimethylformamide, N,N-dimethylacetamide and N,N-dimethylimidazolidinone; ethers such as dibutyl ether, ethylene glycol dimethyl ether, ethylene glycol diethyl ether, diethylene glycol dimethyl ether, diethylene glycol diethyl ether, anisole, phenetole, methoxytoluene, benzyl ether and diphenyl ether; ketones such as heptanone and diisobutyl ketone; and esters such as amyl formate, n-amyl acetate, isoamyl acetate, methylisoamyl acetate, n-butyl acetate, isobutyl acetate, 2-ethylbutyl acetate, methoxybutyl acetate, ethoxyethyl acetate, methoxyethyl acetate, methoxypropyl acetate, ethyl acetate, hexyl acetate, 2-ethylhexyl acetate, cyclohexyl acetate, methylcyclohexyl acetate, benzyl acetate, phenyl acetate, methyl Carbitol acetate, ethylene glycol diacetate, ethyl propionate, n-butyl propionate, isoamyl propionate, ethyl butyrate, butyl butyrate, isoamyl butyrate, butyl stearate, butyl lactate, amyl lactate, dimethyl phthalate, methyl benzoate and ethyl benzoate. Among these, media which are liquid under normal pressure at an appropriate reaction temperature of 90° C. or higher are preferred in view of the economy of reaction facilities. Of these, esters are particularly preferred because they can act to suppress formation of byproducts called "chlorinated derivatives" in which the isocyanate groups are partly or wholly substituted by chlorine atoms.

These solvents can be used either singly or in combination. From the standpoint of recovery for reutilization, however, it is preferred to use them singly.

The liquid medium can be used preferably 3-40 times by weight or, more preferably, 4-20 times by weight of the aliphatic polyamine or its salt. Although an amount smaller than 3 times by weight does not necessarily mean that the reaction will be infeasible, it may become difficult to mix and stir the reaction mixture in some instances. Amounts greater than 40 times by weight lead to a deterioration in the volume efficiency, thereby providing no industrial advantage.

The reaction according to the present invention can be conducted in the following manner: (1) an aliphatic polyamine is employed as a raw material and is initially reacted with phosgene in an inert liquid medium at 100 to 130 C and then ramping the temperature to about 150 to about 180° C.; or (2) an aliphatic polyamine is used as a raw material and, subsequent to formation of its salt by its reaction with hydrochloric acid gas or carbon dioxide gas in the solvent, the salt is reacted with phosgene while ramping the temperature of the mixture of the salt and the medium.

In the above-described manner (1), a two-stage reaction is generally carried out in the solvent. In the first stage, phosgene is charged while maintaining the liquid temperature in a range of 100 to 130° C., whereby a reaction on a low temperature side is conducted. Although the advantageous effects can be brought about fully at any temperature substantially higher than 130° C., the decomposition products incurred by prolonged exposure to higher temperatures have a detrimental effect on the overall yield. Further, this low-temperature reaction often gives preferred results when the raw material aliphatic polyamine is also charged concomitantly with phosgene at a rate such that the molar ratio of a functional group (amino groups/$COCl_2$) to the phosgene is between 0.06 and 0.2. In the second stage, the temperature is raised from that in the first stage and reaction at the higher temperature is conducted. The reaction rate tends to become slower at temperatures below 130° C.; the yield tends to drop due to formation of tar at temperatures higher than 180° C. Temperatures outside the above range are therefore not preferred.

In the above-described manner (2), the aliphatic polyamine is first reacted with hydrochloric acid gas or carbon dioxide gas in an inert liquid medium to form the salt of the aliphatic polyamine. The reaction temperature during this salt-forming reaction is preferably 0 to 60° C. Temperatures lower than 0° C. require an unduly large refrigerating facility as in the manner (1) described above, so that the process is no longer industrially advantageous. Like the low-temperature reaction in the above-described manner (1), this salt-forming reaction can bring about preferred results when the raw material aliphatic polyamine is also charged concomitantly with hydrochloric acid gas at a rate such that the molar ratio of a functional group (amino groups/HCl) to the hydrochloric acid gas is between 0.2 and 1.5. Next, after the solid-liquid mixture is heated, phosgene is reacted. The reaction temperature is preferably 150 to 180° C., like the high-temperature reaction in the manner (1).

The present invention may also be carried out by means of a continuous process. In a continuous process, the amine dissolved in solvent is reacted with phosgene or phosgene in solvent by high efficiency mixing. The reaction mixture at 100-130° C. then flows through and continues to react in a tubular reactor or vessel. The reaction mixture is then transferred by pumping, gravity, or pressure to a second reactor that is maintained at a higher temperature, e.g., 150-180° C., to complete conversion of the amine hydrochloride to product. Following complete conversion, the process stream is distilled to remove phosgene and solvent. The crude isocyanate product is then purified by heat treatment and distillation processes to provide a pure diisocyanate product.

In each manner described above, the solvent is eliminated from the reaction mixture, and the residue is then distilled and purified to obtain the aliphatic polyisocyanate.

The following examples are provided to illustrate the present invention. The examples are not intended to limit the scope of the present invention and should not be so interpreted. All percentages are by weight unless otherwise noted.

EXAMPLES

Comparative Example 1

In a 1-L Parr reactor, 310 g of 70 w/w % phosgene in 1,2-dichlorobenzene is heated to 60° C. with 1500 rpm agitation and brought to 350 psig with nitrogen. In a separate vessel, 390 g of 5 w/w % bis(aminomethyl)cyclohexane in 1,2-dichlorobenzene is heated to 60° C. and brought to 462.5 psig with nitrogen. The amine solution is transferred to the agitated phosgene solution through a sub-surface nozzle. The resulting mixture is held at 60° C. and 350 psig for 5 minutes at 1500 rpm, then agitation is reduced to 750 rpm and the reaction temperature is increased to 160° C. When the reaction mixture reaches approximately 80° C., solids agglomerate requiring agitation to be terminated. As the reaction mixture approaches 160° C., normal agitation (750 rpm) is resumed. After 11 hours at 160° C., the reaction is complete as indicated by the disappearance of visible solids.

Following solvent removal, 22 g of liquid are recovered, along with 3 g solids. The liquid is analyzed and determined to be 71 w/w % bis(isocyanatomethyl)cyclohexane (by Gas Chromatograph) and 38.9% NCO.

Example 1

A reaction is conducted in the same manner as in the comparative example 1, except the initial temperature of the phosgene solution and of the amine solution is 130° C. This mixture is held at 130° C. for 5 minutes at 1500 rpm, then agitation is reduced to 750 rpm and the reaction temperature is increased to 160° C. No agglomeration occurs, and agitation is unimpeded. The reaction is complete after 8 hours.

After solvent removal, 23 g of liquid are recovered, along with 3 g solids. The liquid is analyzed and determined to be 80 w/w % bis(isocyanatomethyl)cyclohexane (by Gas Chromatorgaph) and 40% NCO.

| | |
|---|---|
| Initial amine concentration, w/w %: | 3-20 |
| Ratio of phosgene to amine equivalent: | 4-16 |
| Initial phosgene concentration, w/w %: | 35-90 |
| Solvents: | 1,2-dichlorobenzene, chlorobenzene, other aromatic solvents |
| Temperature, ° C. | 120-200 |
| Pressure, psig | 50-400 |
| Reaction time, hrs | 2-20 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A cycloaliphatic isocyanate containing liquid composition obtained from a process comprising:
   reacting a cycloaliphatic primary amine, or the hydrochloride or carbonate salt thereof, with phosgene in the presence of an inert solvent wherein the initial reaction temperature is between 100 and 130° C. and within 60 minutes of reaching said reaction temperature,
   subsequently increasing the temperature to 150 to 180° C. during the course of the reaction over a time span of about 10 minutes or less,
   maintaining the solvent to amine weight ratio from 95:5 to 80:20,
   maintaining the total reaction pressure between 50 and 350 psig and
   dispersing the amine in the phosgene;
   wherein the cycloaliphatic amine is selected from the group consisting of 1,3-bis(aminoethyl)cyclohexane, 1,4-bis(aminomethyl)cyclohexane, bis(aminoethyl)cyclohexane, 1,4-diaminocyclohexane, 2,4,6-tri(aminomethyl)cyclohexane, isophoronediamine, bis(aminocyclohexyl)methane, 2,2-bis(aminomethy)propane, bis(aminomethy)cyclohexane, bis(aminomethyl)norbornene, and isomeric mixtures thereof; and
   wherein the cycloaliphatic isocyanate containing liquid composition comprises, following solvent removal and in the absence of any further separation steps, 80 w/w % or greater, but less than 100 w/w % of cycloaliphatic isocyanate, and balance unreacted phosgene and chlorinated byproducts.

2. The cycloaliphatic isocyanate of claim 1 wherein the amine is dispersed in the phosgene through injection.

3. The cycloaliphatic isocyanate of claim 1 wherein phosgene is used as a co-solvent.

4. A cycloaliphatic isocyanate containing liquid composition obtained from a process comprising:
   reacting an aliphatic or cycloaliphatic amine, or the hydrochloride or carbonate salt thereof, with phosgene in the presence of an inert solvent wherein the reaction is done in two or more sequential reactors,
   maintaining reactor temperature from 100 to 130° C.,
   controlling the solvent to amine weight ration is 95:5 to 80:20, and the total reactor pressure from 50 to 350 psig and
   providing a residence time in the first reactor of less than 5 minutes;
   transferring the product from a first reactor into a second reactor,
   maintaining a temperature in the second reactor from 150 to 180 C,
   controlling a total second reactor pressure from 50 to 350 psig and
   providing a residence time in the second reactor of less than 8 hours;
   wherein the cycloaliphatic amine is selected from the group consisting of 1,3-bis(aminomethyl)cyclohexane, 1,4-bis(aminomethyl)cyclohexane, bis(aminoethyl)cyclohexane,1,4-diaminocyclohexane, 2,4,6-tri(aminomethyl)cyclohexane, isophoronediamine, bis(aminocyclohexyl)methane, 2,2-bis(aminocyclohexyl)propane, bis(aminomethyl)cyclohexane, bis(aminomethyl)norbornene, and isomeric mixtures thereof; and
   wherein the cycloaliphatic isocyanete containing liquid composition comprises, following solvent removal and in the absence of any further seperation steps, 80 w/w % or greater, but less than 100 w/w % of cycloaliphatic isocyanate, and balance unreacted phosgene and chlorinated byproducts.

5. The cycloaliphatic isocyanate of claim 4, wherein the amine is dispersed in the phosgene through injection.

6. The cycloaliphatic isocyanate of claim 1, wherein the aliphatic or cycloaliphatic amine is composed of an isomeric mixture of amines.

7. The cycloaliphatic isocyanate of claim 1, wherein the cycloalipahtic amine is selected from the group consisting of 1,3-bis(aminomethyl)cyclohexane, 1,4-bis (aminomethyl) cyclohexane or an isomeric mixture thereof.

8. The cycloaliphatic isocyanate according to claim 1, wherein the cycloaliphatic amine is selected from the group consisting of bis(aminoethyl)cyclohexane,1,4-diaminocyclohexane, 2,4,6-tri(aminomethyl)cyclohexane, isophoronediamine, bis(aminocyclohexyl)methane, 2,2-bis(aminocyclohexyl)propane, bis(aminomethyl)cyclohexane and bis(aminomethyl)norbornene.

9. The cycloaliphatic isocyanate according to claim 1, wherein the reaction is conducted in an inert liquid medium having a boiling point of 90° C. or higher.

10. The cycloaliphatic isocyanate according to claim 1, wherein the inert liquid medium is an organic solvent having a donor number greater than 7.

\* \* \* \* \*